US00PP37258P2

(12) United States Plant Patent
Erhart

(10) Patent No.: US PP37,258 P2
(45) Date of Patent: Feb. 10, 2026

(54) ***HIBISCUS* PLANT NAMED 'WALHIDELI'**

(50) Latin Name: ***Hibiscus paramutabilis* x *syriacus***
Varietal Denomination: WALHIDELI

(71) Applicant: Walberton Plants Limited, Walberton (GB)

(72) Inventor: Eva Erhart, Walberton (GB)

(73) Assignee: Wallburton Plants Limited (GB)

( * ) Notice: Subject to any disclaimer, the term of this patent is extended or adjusted under 35 U.S.C. 154(b) by 0 days.

(21) Appl. No.: 19/185,633

(22) Filed: Apr. 22, 2025

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
See application file for complete search history.

(56) References Cited

PUBLICATIONS https://amateurgardening.com/how-to/sensational-shrubs/ Retrieved from the Internet on Jun. 17, 2025.*
https://www.landscaping.co.uk/products/hibiscus-syr-walbertonsr-lunar-delight-pbr-trees?srsltid=AfmBOopV4qP3rycuTnMXIGnzwZALI2AIQ79sxGB-0AzbdJAfWTczzqPF—Retrieved from the Internet on Jun. 17, 2025.*

* cited by examiner

*Primary Examiner* — Susan McCormick Ewoldt

(57) ABSTRACT

A new and distinct cultivar of *Hibiscus* plant named 'WALHIDELI' is disclosed, characterized by large, purple-red to purple-pink flowers with a deep red "eye". Plants are winter-hardy and have broadly upright habits. The new variety is a *Hibiscus*, typically produced as an ornamental plant.

2 Drawing Sheets

Latin name of the genus and species: *Hibiscus paramutabilis* x *syriacus*.

Variety denomination: 'WALHIDELI'.

BACKGROUND OF THE INVENTION

The new *Hibiscus* cultivar is a product of a planned breeding program by the inventor. *Hibiscus* 'WALHIDELI' is the result of an open pollination of the seed parent, unpatented *Hibiscus* '03S24 SALM', a proprietary, unreleased selection. The pollen parent in unknown. The crossing resulting in this new variety was made during 2015 at a nursery in Walberton, United Kingdom.

The new cultivar was found and selected by the inventor in a group of seedlings at the same nursery in Walberton, United Kingdom during 2016.

Asexual reproduction of the new cultivar 'WALHIDELI' was first performed in July of 2019 in Walberton, United Kingdom, by softwood cuttings. Subsequent propagation has shown that the unique features of this cultivar are stable and reproduced true to type in successive generations.

SUMMARY OF THE INVENTION

The cultivar 'WALHIDELI' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'WALHIDELI'. These characteristics in combination distinguish 'WALHIDELI' as a new and distinct *Hibiscus* cultivar:

1. Larger flowers.
2. Strongly upright habit.
3. Winter hardiness to at least −10° C.
4. Petaloids present.

PARENT COMPARISON

Plants of 'WALHIDELI' are similar in some horticultural characteristics to the seed parent. The new variety, however, differs in the following:

1. Flower color of the new variety is purple-red to purple-pink, while the flower color of the seed parent is salmon-pink.

COMMERCIAL COMPARISONS

Plants of 'WALHIDELI' are similar in some horticultural characteristics to the variety *Hibiscus* 'WALHIROSMO', U.S. Plant Pat. No. 24,936. The new variety, however, differs in the following:

1. Flowers of the new variety have petaloids, while flowers of this comparator do not have petaloids.
2. Petals of the new variety overlap, while petals of this comparator do not overlap.
3. Flower color of the new variety is between RHS Purple-Red 186B and 186C, while the flower color of this comparator is Red-Purple N78B.

Plants of 'WALHIDELI' are similar in some horticultural characteristics to the variety *Hibiscus* 'Woodbridge', unpatented. The new variety, however, differs in the following:

1. Flowers of the new variety are much larger than flowers of this comparator.
2. Petals of the new variety overlap, while petals of this comparator do not overlap.
3. Flowers of the new variety have petaloids, while flowers of this comparator do not.

BRIEF DESCRIPTION OF THE PHOTOGRAPHS

Figure 1:
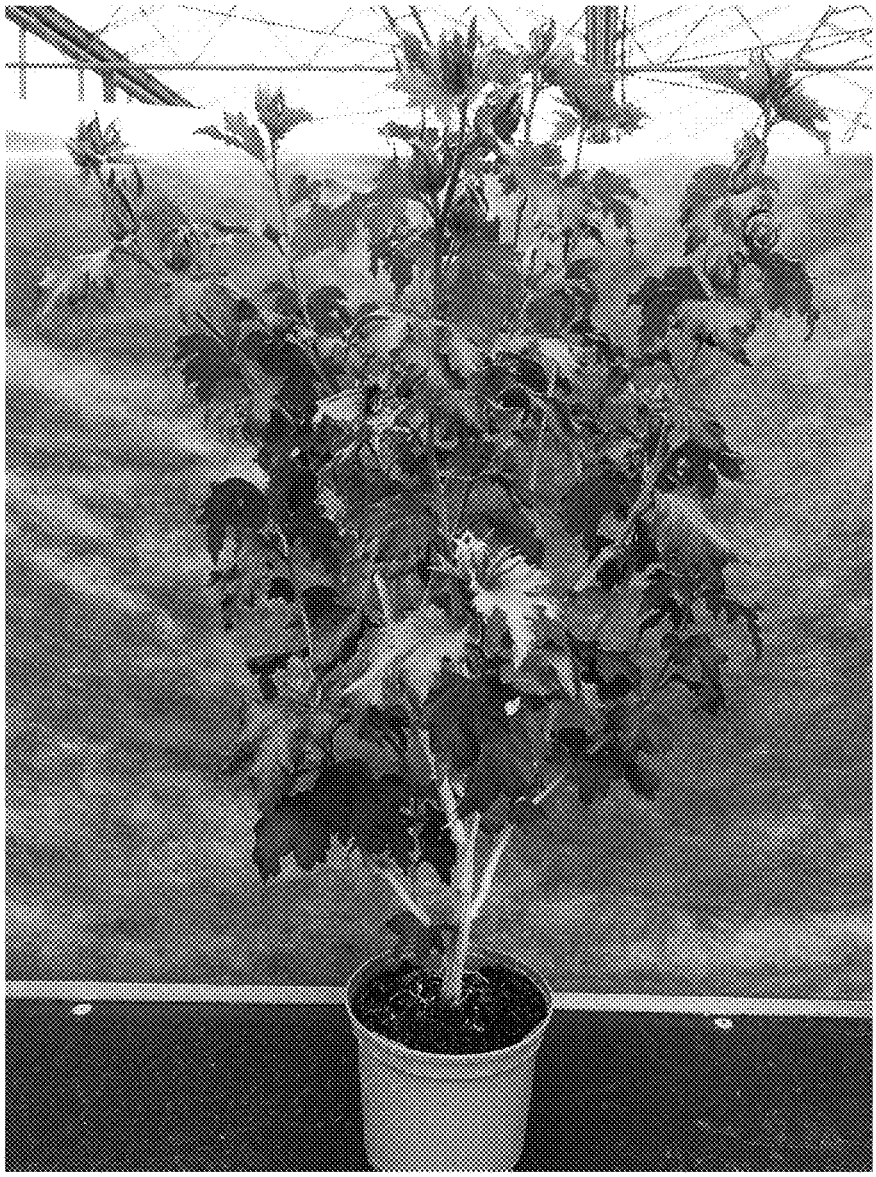

The accompanying photograph in FIG. 1 illustrates in full color a typical plant of 'WALHIDELI' grown in an unheated glasshouse at a nursery in Walberton, United Kingdom. This plant is approximately 2 years old, shown in a 2 liter container.

Figure 2:
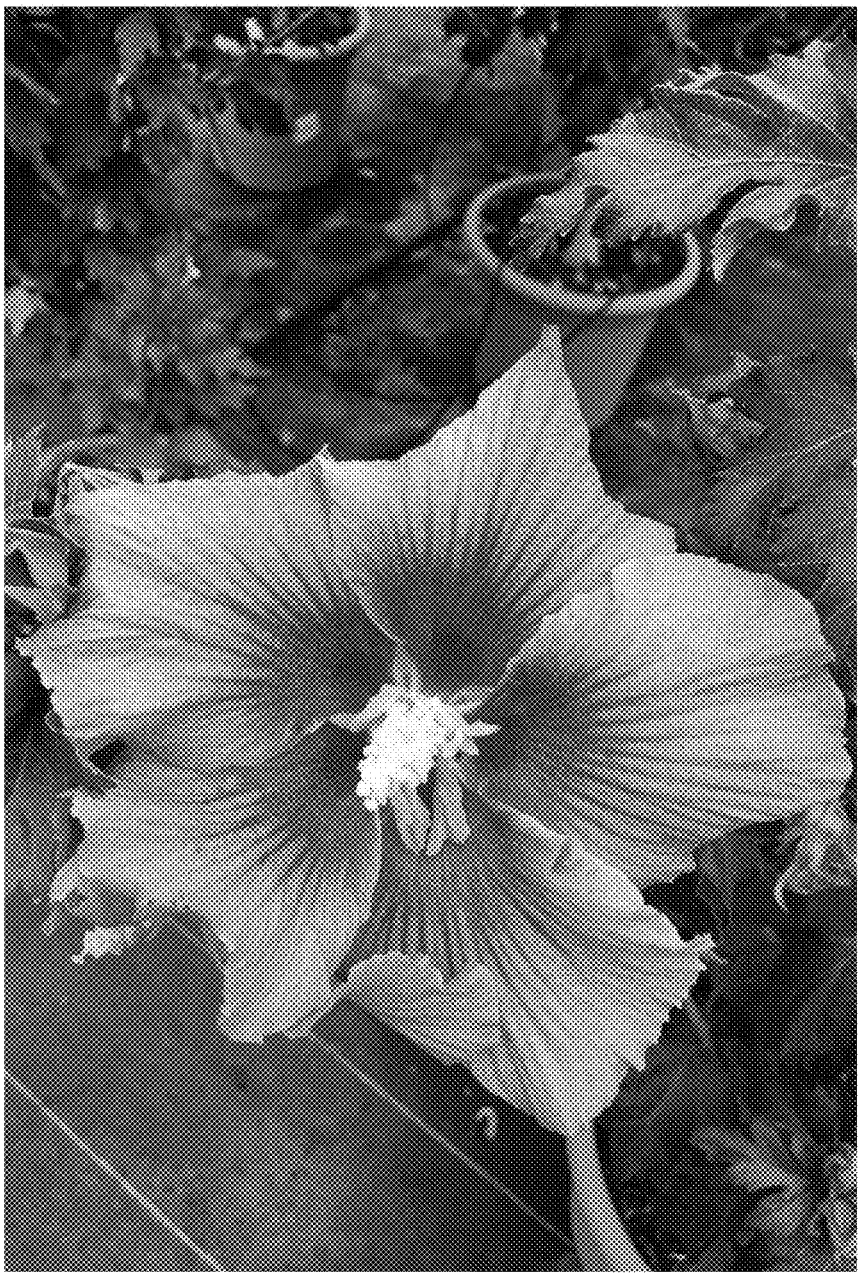

FIG. 2 illustrates a closer view of the flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe a 'WALHIDELI' plant. This plant is approximately 3 years old, shown in a 1.5 liter container. Temperatures ranged from 0° C. to 33° C. during the day to −8° C. to 18° C. at night. No artificial light, photoperiodic treatments were given to the plants. Measurements and numerical values represent averages of typical plant types.

Botanical classification: *Hibiscus paramutabilis* x *syriacus* 'WALHIDELI'.

PROPAGATION

Time to initiate roots: 20 to 24 days in summer; 14 to 18 weeks in winter at 0° C. to 33° C.

Root description: Fine, fibrous.

PLANT

Plant type: Deciduous flowering shrub.

Age of plant described: 3 years old.

Growth habit: Strongly upright, broadening slightly with age.

Growth rate: Moderate.

Height: 65 cm.

Plant spread: 38 cm.

Branching characteristics:

Primary lateral branches:

*Quantity*.—Typically 6.

*Length*.—35 to 42 cm.

*Diameter*.—0.65 cm, tapering to 0.4 cm near apex.

*Shape*.—Virgate, upright.

*Strength*.—Stiff, strong.

*Color*.—Between RHS Olive-Gray 197A and 197B.

*Texture*.—Verrucose.

Internode length: 3.2 to 6 cm.

FOLIAGE

Leaf:

*Arrangement*.—Alternate, spirally arranged, dextrorse; leaves held singly, rarely in pairs at lower (older) nodes.

*Quantity*.—10 to 19 per branch.

*Average length*.—13.9 cm.

*Average width*.—11.8 cm.

*Shape of blade*.—Palmatifid, three-lobed.

*Apex*.—Acute.

*Base*.—Broadly cuneate to hastate; mature leaves hastate.

*Margin*.—Serrate, teeth 0.5 to 0.6 cm deep. Lower quarter of each lobe more or less.

*Texture of top surface*.—Areolate.

*Texture of bottom surface*.—Areolate, very sparsely hispid.

*Aspect*.—Petiole held 70° to 90° from stem.

*Color*.—Young foliage upper side: RHS Yellow-Green 147A. Young foliage under side: RHS Yellow-Green 147B. Mature foliage upper side: RHS Green NN 137A. Mature foliage under side: RHS Green NN 137B. Autumn color upper side: RHS Yellow 13A. Autumn color under side: RHS Yellow 13C.

*Venation*.—Type: Palmate. Venation color, upper side: RHS Yellow-Green 147B. Venation color, under side: RHS Yellow-Green 146C.

*Petiole*.—Length: 6.3 cm. Diameter: 0.2 cm. Color: RHS Green 139B. Texture: Rugose.

FLOWER

Natural flowering season: May to September at the breeder's location.

Flower type and habit: Solitary, rotate. Single with petaloids. Petals overlapping.

Rate of flower opening: 2 to 3 days from bud dehiscence (cracking color) to fully opened flower.

Flower longevity on plant: 2 to 3 days.

Persistence: Self-cleaning.

Fragrance: None.

Bud:

*Shape*.—Broadly ovate.

*Length*.—3.2 cm.

*Diameter*.—1.9 cm at widest.

*Apex*.—Acute to attenuate.

*Base*.—Rounded.

*Texture*.—Scabrid to verrucose.

*Color*.—Between RHS Yellow-Green 147C and 148C.

Flower Size:

*Diameter*.—16.2 cm.

*Depth*.—6.5 to 7.0 cm from base to tip of stamen stalk.

Petals:

*Quantity*.—5.

*Arrangement*.—Rotate.

*Length*.—8.2 cm at longest part.

*Width*.—6 7.2 cm at widest.

*Shape*.—Orbicular to obovate.

*Apex*.—Rounded.

*Base*.—Obtuse.

*Margin*.—Undulate and crisped, revolute.

*Texture, upper and lower surfaces*.—Glabrous, slightly shiny, especially the eye area.

*Color*.—Eye-size and feathering: Extends 30% to 50% of length of petal from petal base, medium to significant feathering. Petal color on bud at point of color cracking: RHS Purple-Red 64B. Fully opened, upper surface, main color: Between RHS Purple-Red 186B and Purple-Pink 186C. Fully opened, upper surface, eye color: RHS Red 187C. Fully opened, lower surface: Between RHS Purple-Pink 68B and 68C; veins White N 155A; base White N 155A.

Petaloids:

*Quantity*.—Varies; typically 5.

*Arrangement*.—Rotate; attached approximately 0.5 cm up stamen stalk.

*Length*.—1.4 to 2.3 cm.

*Width*.—0.4 to 0.8 cm.

*Shape*.—Obovate; whole petaloid is undulate to contorted and twisted.

*Apex*.—Obtuse to acute.

*Base*.—Attenuate.

*Margin*.—Entire at sides; apex crenate to crenulate.

*Texture, upper and lower surfaces*.—Glabrous, slightly shiny.

*Color*.—Fully opened, upper surface: RHS Purple-Red 75B; White N 155A at base. Fully opened, lower surface: RHS Purple-Red 75B; White N 155A at base.

Calyx sepals:

*Quantity*.—4 to 6, typically 5.

*Length*.—3.2 to 3.4 cm.

*Width*.—1.6 to 1.9 cm at widest part.

*Shape* (*overall*).—Broadly lanceolate, campanulate, fused for lower third. Apex: Acute to attenuate. Base: Truncate, fused.

*Margin*.—Entire.

*Color*.—Between RHS Yellow-Green N 148B and N 148C.

*Texture*.—Scabrid.

Epicalyx sepals:

*Quantity*.—5 or 6.

*Length*.—3.5 to 3.8 cm.

*Width*.—0.5 to 0.6 cm at widest part.

*Shape* (*overall*).—Linear-lanceolate, fused at base; campanulate overall.

*Apex*.—Acute to attenuate.

*Base*.—Truncate, fused.

*Margin*.—Entire.

*Color*.—RHS Yellow-Green 148B; 147B at base.

*Texture*.—Scabrid.

Peduncle:

*Length*.—2.4 cm.

*Diameter*.—0.4 cm.

*Angle*.—60° to 70° to the lateral branch.

*Strength*.—Strong, rigid.

*Texture*.—Scabrid to strigose.

*Color*.—RHS Yellow-Green N148B.

REPRODUCTIVE ORGANS

Stamen stalk:

*Length*.—4 cm.

*Diameter*.—0.4 cm at base, tapering to 0.25 cm near apex.

*Color*.—Between RHS White NN 155D and pure white.

*Protruding beyond petals*?.—Yes, in fully opened flowers.

Stamens:

*Quantity*.—Typically between 50 and 65.

*Arrangement on stalk*.—6 to 7 whorls.

Anthers:

*Shape*.—Globular.

*Length*.—Approximately 0.1 to 0.2 cm.

*Color*.—RHS White NN 155D.

*Pollen*.—Color: RHS Yellow 12D. Quantity: Very little.

Pistil:

*Number*.—5.

*Length*.—0.6 cm. Style.—Length: 0.4 cm. Color: Between RHS Yellow-Green 150D and 154D.

*Stigma*.—Shape: Oblately globular. Color: RHS White 155B. Ovary Color: Between RHS Yellow-Green 150D and 154D.

OTHER CHARACTERISTICS

Seeds: Not observed.

Disease/pest resistance: Neither resistance nor susceptibility to normal diseases and pests of *Hibiscus paramutabilis* x *Hibiscus syriacus* have been observed.

Temperature tolerance: Trialed without adverse effect at temperatures ranging −10° C. to 45° C.

What is claimed is:

1. A new and distinct cultivar of *Hibiscus* plant named 'WALHIDELI' as herein illustrated and described.

* * * * *